(12) United States Patent
Fujimori et al.

(10) Patent No.: US 7,946,983 B2
(45) Date of Patent: May 24, 2011

(54) BODY-INSERTABLE APPARATUS AND POWER SUPPLYING METHOD THEREFOR

(75) Inventors: Noriyuki Fujimori, Suwa (JP); Takemitsu Honda, Hino (JP)

(73) Assignees: Olympus Medical Systems Corp., Tokyo (JP); Olympus Corporation, Tokyo (JP)

( * ) Notice: Subject to any disclaimer, the term of this patent is extended or adjusted under 35 U.S.C. 154(b) by 943 days.

(21) Appl. No.: 11/639,080

(22) Filed: Dec. 14, 2006

(65) Prior Publication Data

US 2007/0171013 A1   Jul. 26, 2007

(30) Foreign Application Priority Data

Dec. 14, 2005   (JP) ................... 2005-360775

(51) Int. Cl.
*A61B 1/00* (2006.01)
*A61B 5/07* (2006.01)
(52) U.S. Cl. ........ 600/302; 600/101; 600/121; 335/151; 335/205
(58) Field of Classification Search .................. 600/302, 600/101–103, 109, 118, 119, 121, 122, 160, 600/407, 424, 117; 335/151–153, 205–207
See application file for complete search history.

(56) References Cited

U.S. PATENT DOCUMENTS

| | | |
|---|---|---|
| 2004/0215059 A1 | 10/2004 | Homan et al. |
| 2004/0254455 A1 | 12/2004 | Iddan |
| 2008/0103372 A1 * | 5/2008 | Segawa .................. 600/302 |

FOREIGN PATENT DOCUMENTS

| | | |
|---|---|---|
| JP | 2003-185485 | 7/2003 |
| JP | 2003-210395 | 7/2003 |
| JP | 2004-321605 | 11/2004 |
| JP | 2005-237460 | 9/2005 |
| WO | WO 2005/072068 A2 | 8/2005 |

OTHER PUBLICATIONS

Chinese Office Action dated Oct. 9, 2009.
Extended Supplementary European Search Report dated Mar. 15, 2011.

* cited by examiner

*Primary Examiner* — Ramon A Barrera
(74) *Attorney, Agent, or Firm* — Scully, Scott, Murphy & Presser, P.C.

(57) ABSTRACT

An object of the present invention is to easily start to operate a body-insertable apparatus which is introduced into a subject and executes a predetermined function. In a capsule endoscope 3 of the invention, a magnetic switch 14 is arranged in a tubular capsule casing 16 of the capsule endoscope 3 in a direction substantially perpendicular to a longitudinal axis t direction of the capsule casing 16. A movable electrode of the magnetic switch 14 is brought into contact with a fixed electrode of the magnetic switch by a magnetic induction action by a magnetic field generated by a magnet 6, which is applied to the magnetic switch 14 from the outside of the capsule endoscope 3 in a direction substantially parallel to the longitudinal axis t direction of the capsule casing 16. As a result, electric power can be supplied from a power source unit to a function executing unit.

6 Claims, 6 Drawing Sheets

BODY-INSERTABLE APPARATUS AND POWER SUPPLYING METHOD THEREFOR

CROSS-REFERENCE TO RELATED APPLICATIONS

This application is based upon and claims the benefit of priority from Japanese Patent Application No. 2005-360775, filed Dec. 14, 2005, the entire contents of which are incorporated herein by reference.

BACKGROUND OF THE INVENTION

1. Field of the Invention

The present invention relates to a body-insertable apparatus, such as a capsule endoscope, which is introduced into a subject and is operated by electric power supplied to execute predetermined functions, and a power supplying method therefor.

2. Description of the Related Art

Recently, in the field of endoscopes, there is proposed a swallowable capsule endoscope. The capsule endoscope has imaging and radio communication functions. During a period from a time when the capsule endoscope is swallowed from the mouth into a subject (human body) for the observation (examination) to a time when the endoscope is ordinary excreted from the body, the capsule endoscope peristaltically moves in the body cavity, or inside the internal organs, such as stomach and small intestine, and successively picks up images in the body cavity.

Image data picked up by the capsule endoscope in the body cavity during the movement of the endoscope in the body cavity are successively transmitted by radio communication to an external device and stored in a memory of the external device. The subject is allowed to freely act without constraint while carrying a receiving device having radio communication and memory functions during a period from a time when the subject swallows the capsule endoscope to a time when the endoscope is excreted from the body. After the capsule endoscope is excreted, a doctor or a nurse displays images of internal organs on a display screen according to the image data stored in the memory and diagnoses the subject (for example, Japanese Patent Application Laid-Open No. 2003-210395).

A reed switch, which operates responsive to an externally applied magnetic field, is sometimes used for turning on the power source to supply electric power to function executing units. In general, in use, the extending direction of an existing reed switch must be aligned with the direction of the magnetic field applied.

However, the capsule endoscope is rotationally symmetric in shape with respect to the longitudinal axis direction and no rule is applied to its rotational directions. The fact makes it difficult to align the direction of the magnetic field with the extending direction of the reed switch. For this reason, to operate the reed switch, the directivity must be checked by, for example, rotating a magnet for generating the magnetic field around the reed switch. The on/off operation of the reed switch is troublesome and cumbersome.

SUMMARY OF THE INVENTION

At least one object of the present invention is to solve the problems.

A body-insertable apparatus according to one aspect of the present invention includes a function executing unit which executes a predetermined function; a power source unit which supplies electric power to the function executing unit; a capsule body which contains the function executing unit and the power source unit; and a magnetic switch which is provided in the capsule body, and controls the power supply from the power source unit to the function executing unit by a pair of contacts, the pair of contacts being brought into contact with or separated from each other by a magnetic field, the magnetic field being applied from the outside of the capsule body in a direction substantially parallel to a longitudinal axis direction of the capsule body.

A body-insertable apparatus according to another aspect of the present invention includes a function executing unit which executes a predetermined function; a power source unit which supplies electric power to the function executing unit; a switch unit which disconnectively connects the function executing unit and the power source unit; and a capsule body which is tubular and rotationally symmetric with respect to a longitudinal axis direction, and contains the function executing unit, the power source unit, and the switch unit. The switch unit is provided perpendicular to the longitudinal axis direction, and controls the power supply from the power source unit to the function executing unit in accordance with an action of a magnetic field, the magnetic field being applied from the outside of the capsule body in a direction substantially parallel to the longitudinal axis direction.

A power supplying method for a body-insertable apparatus according to still another aspect of the present invention includes a switch arrangement step of arranging a switch unit which is connected to between a function executing unit for executing a predetermined function and a power source unit for supplying electric power to the function executing unit in a capsule body, the capsule body being tubular and rotationally symmetric with respect to a longitudinal axis direction in a state that the switch unit is oriented perpendicular to the longitudinal axis direction; and a power supply step of applying a magnetic field to the switch unit from the outside of the capsule body in a direction substantially parallel to the longitudinal axis direction to operate the switch unit responsive to an action of the magnetic field and to supply electric power from the power source unit to the function executing unit.

A power supplying method for a body-insertable apparatus according to still another aspect of the present invention includes a switch arrangement step for arranging a switch unit for inputting a signal to a state holding circuit for controlling power supply to a function executing unit for executing a predetermined function in a capsule body, the capsule body being tubular and rotationally symmetric with respect to a longitudinal axis direction in a state that the switch unit is oriented perpendicular to the longitudinal axis direction; and a power supply step for applying a magnetic field to the switch unit from the outside of the capsule body in a direction substantially parallel to the longitudinal axis direction to operate the switch unit responsive to an action of the magnetic field and to input a signal to the state holding circuit to thereby hold a state of the power supply from the power source unit to the function executing unit in accordance with an output of the state holding circuit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
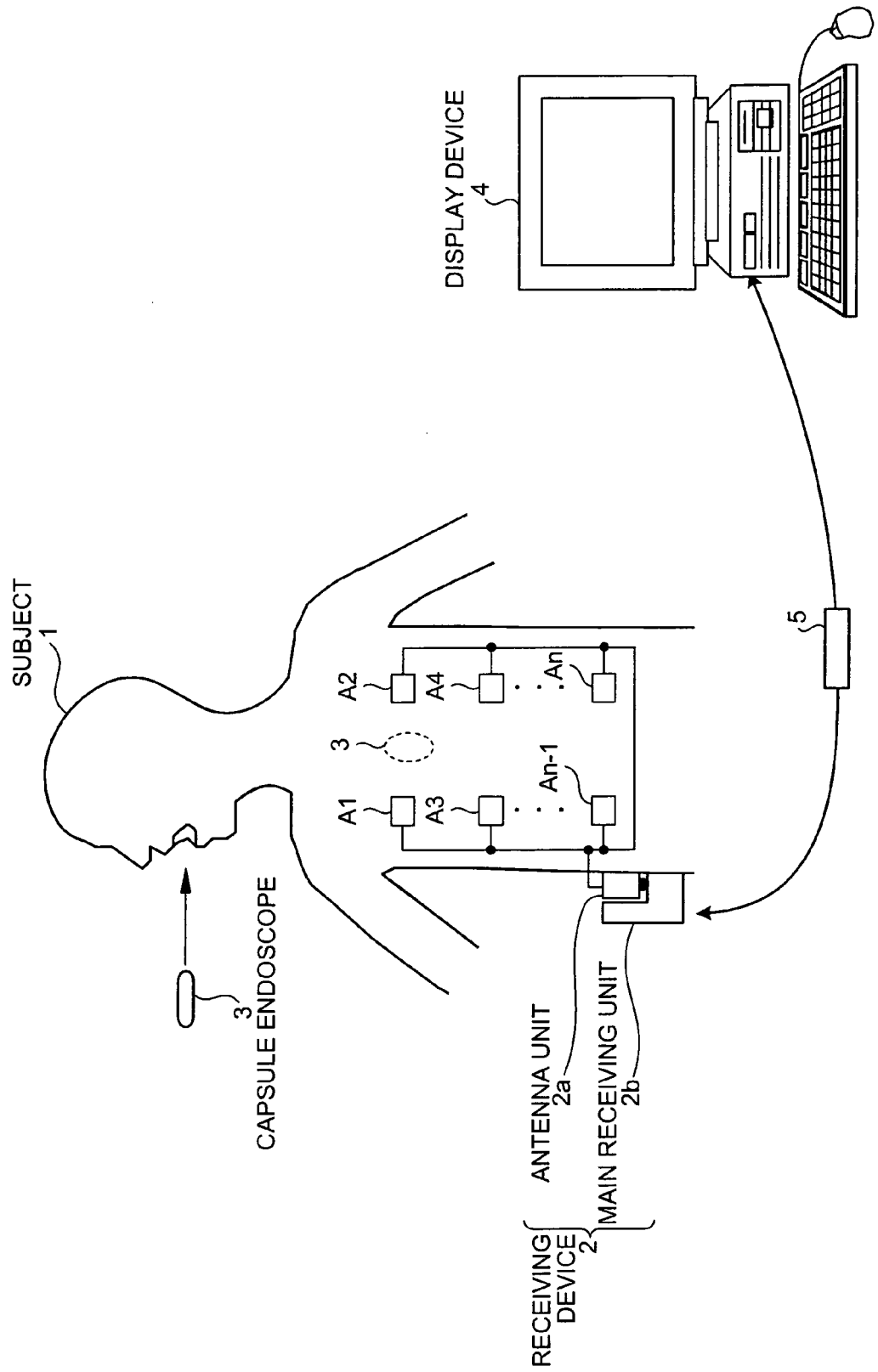
FIG. 1 is a schematic diagram showing an entire configuration of a radio in-vivo information acquiring system including a body-insertable apparatus according to the present invention.

Preferred embodiments of a body-insertable apparatus and a power supplying method therefor according to the present invention will be described in detail below with reference to FIGS. 1 to 10. It should be understood that the invention is not limited to those embodiments, but may be variously modified, varied and changed within the subject matter of the invention.
First Embodiment FIG. 1 is a schematic diagram showing an entire configuration of a radio in-vivo information acquiring system including a body-insertable apparatus according to the invention. The body-insertable apparatus, which is incorporated in the radio in-vivo information acquiring system, will be described by using, by way of example, an capsule endoscope which is introduced from the mouth of a human being as a subject into the body cavity, and images sites to be examined in the body cavity. In FIG. 1, the radio in-vivo information acquiring system includes a receiving device 2 having a radio receiving function, and a capsule endoscope 3 which is inserted into a subject 1, picks up an image in the body cavity, and sends data signals such as image signals to the receiving device 2. The radio in-vivo information acquiring system further includes a display device 4 for displaying the image in the body cavity on the basis of the image signals received by the receiving device 2, and a portable recording medium 5 for transferring data between the receiving device 2 and the display device 4.

The receiving device 2 includes an antenna unit 2a having a plurality of receiving antennas A1 to An to be stuck to an outer surface of the subject 1, and a main receiving unit 2b for performing, for example, signal processing of radio signals received through the receiving antennas A1 to An. These units are detachably connected through connectors or the like. The receiving antennas A1 to An are attached to, for example, a jacket wearable by the subject 1. The receiving antennas A1 to An may be attached to the subject 1 when the subject 1 wears the jacket. In this case, the receiving antennas A1 to An may be detachably attached to the jacket. Additionally, the receiving antennas A1 to An may be housed in an antenna pad designed so as to allow main antenna units provided at the ends of the receiving antennas A1 to An to be attached the body of the subject 1.

The display device 4 such as a work station is used for displaying images in the body cavity picked up by the capsule endoscope 3, and displays images on the basis of data obtained by the portable recording medium 5. Specifically, the display device 4 may be configured such that images are directly displayed by using a CRT display device, a liquid crystal display device or the like. Further, the display device 4 may be configured so as to output images to another medium by using a device such as a printer.

The portable recording medium 5 is constructed so as to be removably coupled to the main receiving unit 2b and the display device 4, and to output or record information when it is coupled to them. In this embodiment, during a period when the capsule endoscope 3 moves in the body cavity of the subject 1, the portable recording medium 5 is coupled to the main receiving unit 2b and records data transmitted from the capsule endoscope 3. After the capsule endoscope 3 is excreted from the subject 1, namely, after the operation of imaging the interior of the subject 1 is completed, the capsule endoscope is taken out from the main receiving unit 2b and set to the display device 4, and the display device 4 reads out data stored in the portable recording medium 5. In a case where the data is transferred between the main receiving unit 2b and the display device 4 by using the portable recording medium 5, which is constructed with, for example, a CompactFlash® memory, the subject 1 is more freely movable during the imaging operation in the body cavity than a case where the main receiving unit 2b and the display device 4 are directly connected to each other by a wire. In the embodiment, the portable recording medium 5 is used for the data transfer between the main receiving unit 2b and the display device 4. In an alternative, another type of memory device of the built-in type, e.g., a hard disk, is used in the main receiving unit 2b, and the wired or radio connection is used for the data transfer to and from the display device 4.

Figure 2:
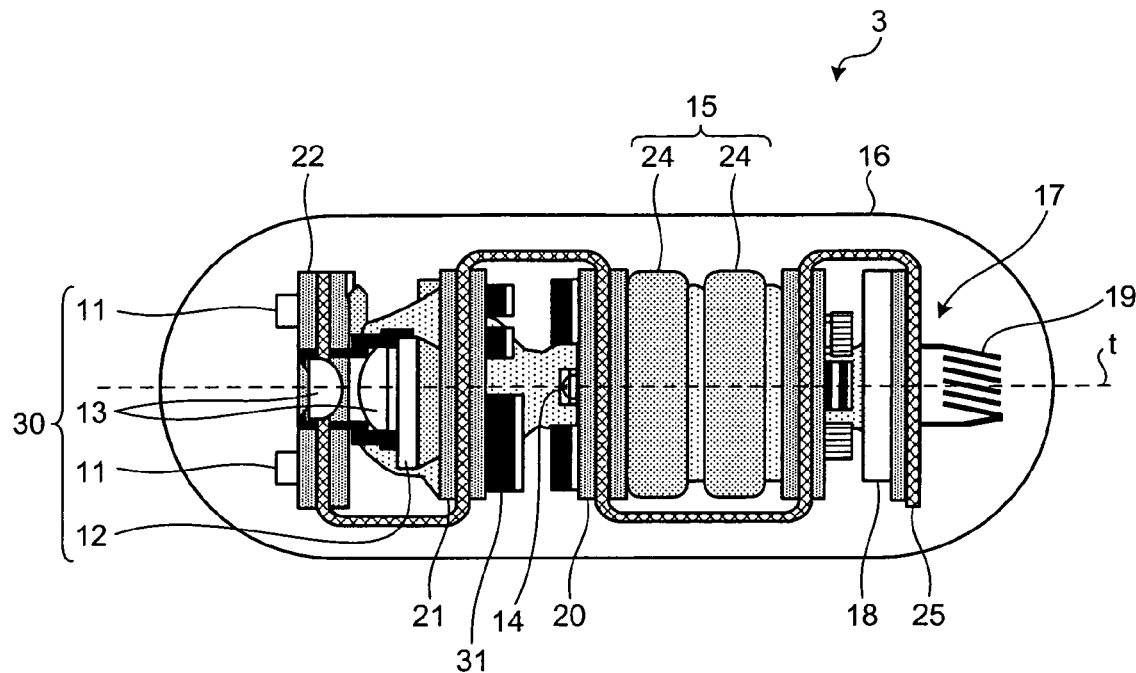
FIG. 2 is a cross sectional view showing an internal configuration of a first embodiment of a capsule endoscope according to the invention.
Figure 3:
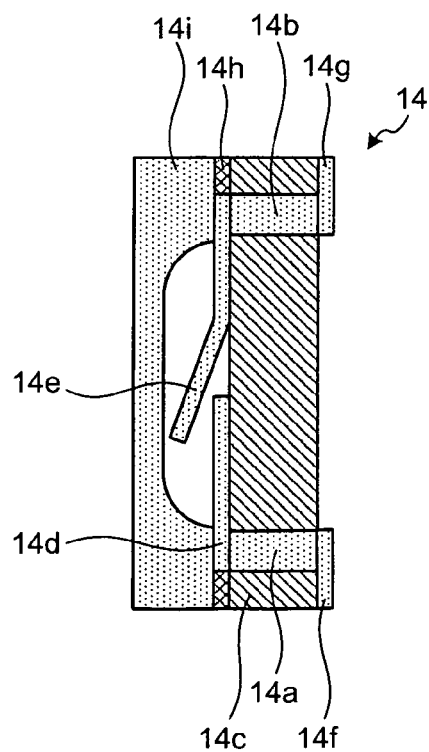
FIG. 3 is an enlarged view showing a configuration of a magnetic switch.
Figure 4:
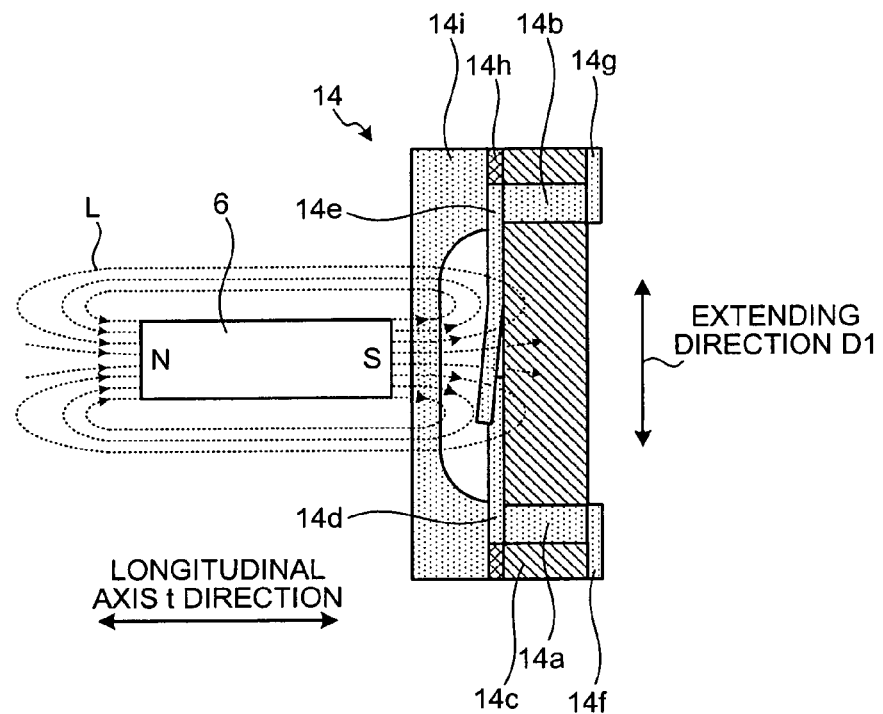
FIG. 4 is an enlarged view showing the configuration of the magnetic switch in a state where a magnet is close to the switch.
Figure 5:
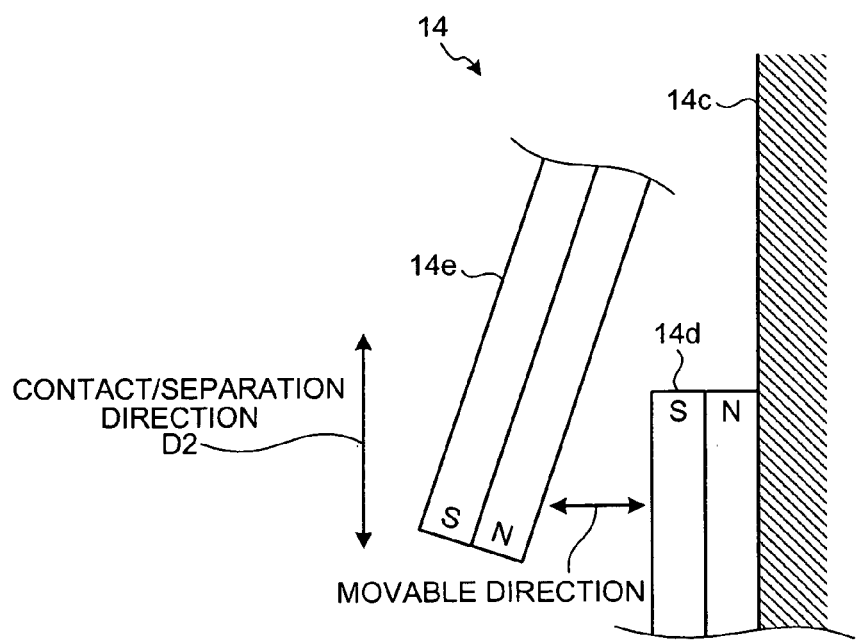
FIG. 5 is a partially enlarged view showing a fixed electrode and a movable electrode of the magnetic switch.
Figure 6:
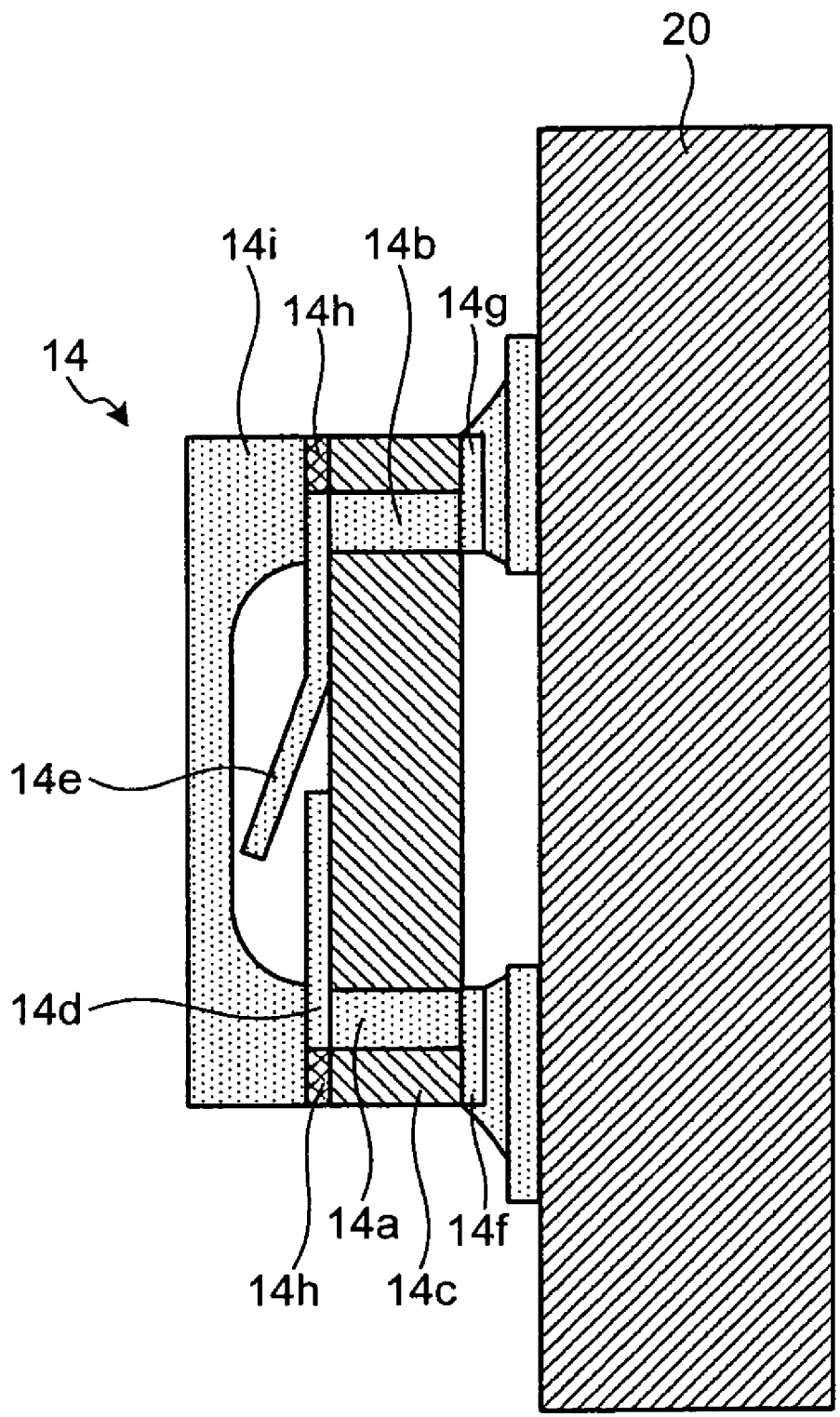
FIG. 6 is an enlarged view showing a configuration of the magnetic switch placed on a switch board.
Figure 7:
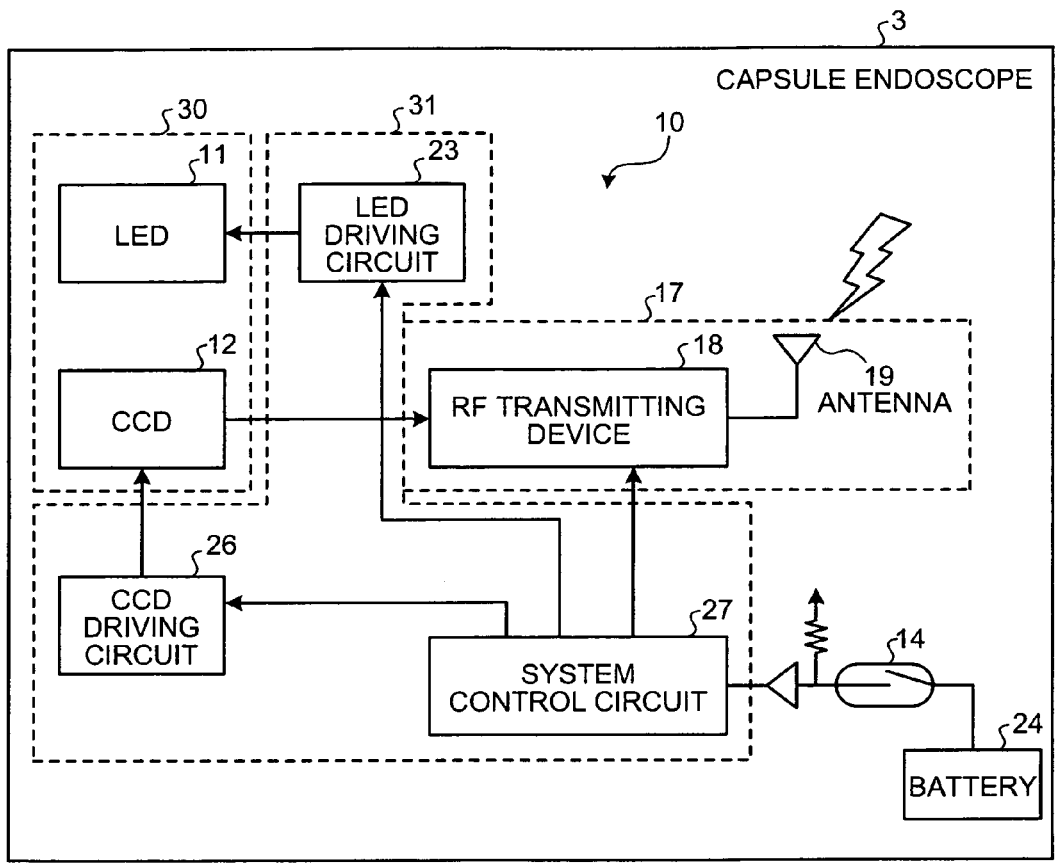
FIG. 7 is a block diagram showing one example of a circuit configuration of the capsule endoscope shown in FIG. 2.

FIG. 2 is a cross sectional view showing an internal configuration of the capsule endoscope 3. FIG. 3 is an enlarged view showing a configuration of a magnetic switch. FIG. 4 is an enlarged view showing the configuration of the magnetic switch when a magnet serving as a magnetic body is moved close to the switch. FIG. 5 is a partially enlarged view showing a fixed electrode and a movable electrode as contacts of the magnetic switch. FIG. 6 is an enlarged view showing a configuration of the magnetic switch placed on a switch board. FIG. 7 is a block diagram showing one example of a circuit configuration of the capsule endoscope 3 shown in FIG. 2. The capsule endoscope 3 has an image sensor 30 as information acquiring means, and a radio unit 17. The image sensor 30 includes LEDs 11 as illuminating means for illuminating the interior of the body cavity of the subject 1, a CCD 12 as imaging means for picking up images in the body cavity, and an optical system device 13 as optical means for forming an image at an imaging position of the CCD 12. The radio unit 17 includes an RF transmitting device 18 as transmitting means for transmitting image data picked up by the CCD 12 and an antenna 19. The image sensor 30 and the radio unit 17 are connected to a power source unit 15 though a magnetic switch 14 in an on and off manner. The power source unit 15 supplies electric power to the image sensor 30 and the radio unit 17 through the magnetic switch 14. These components of the capsule endoscope 3 are housed in a capsule casing 16 as a capsule body. The image sensor 30, the radio unit 17, and a signal processing/control unit 31 to be described later form parts of a function executing unit 10.

The magnetic switch 14, as shown in FIG. 3, is composed of a base seat 14c having through-holes 14a and 14b, a fixed electrode 14d which is provided on the surface of the base seat 14c while contacting the through-hole 14a, a movable electrode 14e which is provided on the surface of the base seat 14c while contacting the through-hole 14b, and is movable to be in contact with the fixed electrode 14d, a reverse-side electrode 14f which is provided on the reverse side of the base seat 14c while contacting the through-hole 14a, and is electrically connected to the fixed electrode 14d through the through-hole 14a, another reverse-side electrode 14g which is provided on the reverse side of the base seat 14c while contacting the through-hole 14b, and is electrically connected to the movable electrode 14e through the through-hole 14b, and a cap 14i which is joined to the surface of the base seat 14c with a joining layer 14h being interposed therebetween, and covers the fixed electrode 14d and the movable electrode 14e. Thus, the magnetic switch 14 forms a so-called surface reaction type magnetic switch. The magnetic switch 14 is 2 mm in length and width and about 0.8 mm in height. A space around the fixed electrode 14d and the movable electrode 14e, which is defined by the base seat 14c and the cap 14i, is filled with inert gas such as nitrogen.

The base seat 14c and the cap 14i are composed of a non-conductive member, and the reverse-side electrodes 14f and 14g are composed of a conductive member. The fixed electrode 14d and the movable electrode 14e are composed of a conductive and magnetic member. The fixed electrode 14d and the movable electrode 14e, as shown in FIGS. 4 and 5, are directly magnetized by a magnetic induction action of a magnetic field L generated by an approaching magnet 6, and thereby to have different magnetic polarities (see FIG. 5) stacked in the electrode thickness direction. Through the magnetization, the movable electrode 14e is movable to and from the fixed electrode 14d.

In the embodiment, the magnetic switch 14 is put on the surface of the switch board 20 located at substantially the central position of a capsule casing 16. An extending direction D1 (see FIG. 4) of the fixed electrode 14d of the magnetic switch 14 is substantially perpendicular to a longitudinal axis t direction of the capsule casing 16 as the capsule body. In the magnetic switch 14, the reverse-side electrodes 14f and 14g, for example, are soldered to wires (not shown) on the switch board 20, and are electrically connected to the function executing unit 10 and a power source unit 15 by way of the wires. Accordingly, when the fixed electrode 14d comes in contact with the movable electrode 14e, electric power is supplied from the power source unit 15 to the function executing unit 10 to thereby enable the respective parts of the function executing unit 10 to operate.

The fixed electrode 14d and the movable electrode 14e of the magnetic switch 14, as shown in FIGS. 4 and 5, are magnetized through the magnetic induction action of the magnetic field L generated by the magnet 6 which approaches the capsule endoscope 3 in the longitudinal axis t direction of the capsule casing 16, whereby those electrodes are moved to come in contact with each other or to separate from each other. In this case, the movable electrode 14e moves in a direction perpendicular to contact/separation direction D2 shown in FIG. 5, so that the movable electrode 14e comes in contact with or separates from the fixed electrode 14d. The contact/separation direction D2 of the movable electrode 14e (i.e., contact/separation direction of the magnetic switch 14), as shown in FIG. 5, is perpendicular to the movable direction of the movable electrode 14e when those are magnetized, and is substantially perpendicular to the longitudinal axis t direction of the capsule casing 16 as the capsule body.

The capsule casing 16 includes a transparent front cover casing shaped like a spherical dome, which covers, for example, the image sensor 30 and the radio unit 17, and a cylindrical body casing which engages with the front cover casing and contains the image sensor 30, the radio unit 17, and the power source unit 15 intervening therebetween in an airtight inner space thereof. A size of the capsule casing 16 is selected such that the subject 1 is easy to swallow it. The body casing is made of a colored material blocking visible light.

The CCD 12 is provided on an imaging board 21 and images an area illuminated by the LEDs 11, and the optical system device 13 contains an image forming lens for forming an object image on the CCD 12. The LEDs 11 are provided on an illumination board 22, and include LEDs located at four positions, which are vertically and horizontally arrayed with respect to the optical axis of the image forming lens. In the image sensor 30, the signal processing/control unit 31 for processing or controlling the related components is provided, as internal control means for controlling the image sensor 30 and the RF transmitting device 18, on the rear side of the imaging board 21. The switch board 20, the imaging board 21, and the illumination board 22 are electrically connected to one another by an appropriate flexible board.

The power source unit 15 includes a button battery 24 having a diameter substantially equal to the inside diameter of the body casing. At least one button battery 24 may be arranged in the capsule casing 16. For example, a silver oxide battery, a charging type battery or a generator type battery may be use for the battery. The RF transmitting device 18 is provided, for example, on the rear side of a radio board 25, and the antenna 19 is provided on the radio board 25, for example.

A circuit configuration of the capsule endoscope 3 will be described below with reference to FIG. 7. The capsule endoscope 3 includes: the image sensor 30 including the LEDs 11 and the CCD 12; the signal processing/control unit 31 including an LED driving circuit 23 for controlling the driving state of the LEDs 11, a CCD driving circuit 26 for controlling the driving state of the CCD 12, and a system control circuit 27 for controlling the operations of the LED driving circuit 23, the CCD driving circuit 26 and the RF transmitting device 18; and the radio unit 17 including the RF transmitting device 18 and the antenna 19.

The capsule endoscope 3, including the system control circuit 27, operates to cause the CCD 12 to acquire image data of a subject site illuminated by the LEDs 11 during a period when the capsule endoscope 3 is introduced into in the subject 1. The acquired image data is converted into an RF signal by the RF transmitting device 18, and transmitted to the outside of the subject 1 through the antenna 19. The capsule endoscope 3 also includes the button batteries 24 for supplying electric power to the system control circuit 27 by way of the magnetic switch 14. The system control circuit 27 has a function to distribute the electric power supplied from the button batteries 24 to other components (LED driving circuit 23, CCD driving circuit 26, RF transmitting device 18).

The following measure may take for the power supply, if necessary. A latch circuit (not shown) is provided between the power source unit 15 and the function executing unit 10. The magnetic switch 14 is arranged as a part of the latch circuit. A signal generated when the fixed electrode 14d and the movable electrode 14e of the magnetic switch 14 are brought into contact with each other as the result of moving the magnet 6 close to those electrodes, is input as a control signal to the latch circuit to set up an on-state (in a state where the fixed electrode 14d and the movable electrode 14e are in contact with each other). Subsequently, this on-state is held by the latch circuit. The electric power fed from the power source unit 15 is continuously supplied to the function executing unit 10. In other words, the magnetic switch 14 may input the signal generated when the fixed electrode 14d and the movable electrode 14e are brought into contact with each other to the latch circuit, and then control the power supply to the function executing unit 10 from the power source unit 15 in accordance with the output signal from the latch circuit. This measure efficiently supplies electric power to the function executing unit while being free from the influence of a contact resistance between the fixed electrode 14d and the movable electrode 14e.

Figure 8:
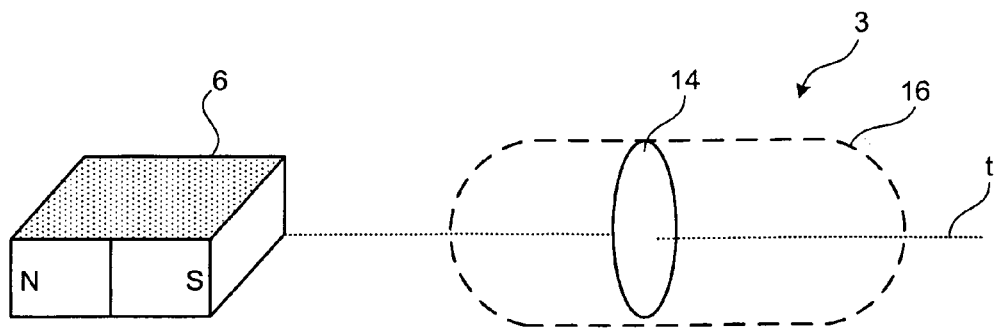
FIG. 8 is a schematic view for explaining a power supplying operation by the magnetic switch.

With such a construction, the external magnet 6, as shown in FIG. 8, is moved close to the magnetic switch 14 in the longitudinal axis t direction of the capsule casing 16 of the capsule endoscope 3 and reaches a position within a range within which the magnetic switch 14 is operable. Then, the fixed electrode 14d and the movable electrode 14e are magnetized by a magnetic induction action of a magnetic field generated by the approaching magnet 6, which acts substantially in parallel with the longitudinal axis t direction, to thereby have different magnetic polarities (see FIG. 5) stacked in the electrode thickness direction. By the magnetization of these electrodes, the movable electrode 14e moves toward the fixed electrode 14d by attraction and comes in contact with the fixed electrode 14d. The power source unit 15 and the function executing unit 10 are electrically connected to each other through the magnetic switch 14, enabling the electric power supply from the power source unit 15 to the function executing unit 10. The magnet 6 may be moved toward the magnetic switch 14 from the leading end of the capsule endoscope 3 containing the image sensor 30 or the trailing end thereof containing the radio unit 17.

Description will be given hereunder about a method of supplying electric power in the capsule endoscope according to the embodiment of the invention. The capsule endoscope 3 is first formed in which the function executing unit 10 (image sensor 30, radio unit 17, signal processing/control unit 31, etc.) and the magnetic switch 14, as shown in FIG. 2, are disposed inside the capsule casing 16. In this case, the magnetic switch 14 having the fixed electrode 14d and the movable electrode 14e, which are brought into contact with or separated from each other when applied with a magnetic field whose direction is perpendicular to the extending direction D1 (see FIG. 4), is placed in the capsule casing 16 of the capsule endoscope 3, which is tubular and rotationally symmetric in shape with respect to the longitudinal axis t direction, such that the extending direction D1 is substantially aligned with the longitudinal axis t direction (switch arrangement step). As already stated, the magnetic switch 14 is electrically connected to the function executing unit 10 and the power source unit 15.

The magnet 6 is moved to or from the magnetic switch 14 from the outside of the capsule endoscope 3, thereby magnetically operating the magnetic switch 14. As a result, electric power is supplied from the power source unit 15 to the function executing unit 10 through the magnetic switch 14 (power supply step). In the power supply step, as shown in FIGS. 4 and 8, the magnet 6 is moved to the magnetic switch 14 from the outside of the capsule endoscope 3 so as to substantially align the direction of the magnetic field generated by the magnet 6 with the longitudinal axis t direction of the capsule casing 16. When the magnet 6 moves and enters the range within which the magnetic switch 14 is operable, the fixed electrode 14d and the movable electrode 14e of the magnetic switch 14 are then magnetized such that the surfaces of those electrodes, which face each other, have different magnetic polarities (S and N polarities), in accordance with the magnetic induction action of the magnetic field generated by the magnet 6, which acts substantially in parallel with the longitudinal axis t direction (viz., substantially perpendicular to the contact/separation direction D2) (see FIG. 5). By the magnetization of these electrodes, the movable electrode 14e moves toward the fixed electrode 14d by attraction and comes in contact with the fixed electrode 14d. As a result, electric power may be supplied from the power source unit 15 to the function executing unit 10 through the magnetic switch 14.

The following approach is allowed in which the magnetic switch 14, as described above, may be provided between the power source unit 15 and the function executing unit 10, and a signal generated when the fixed electrode 14d is brought into contact with the movable electrode 14e is input as a control signal to a latch circuit (not shown) which functions as a state holding circuit for controlling the power supply from the power source unit 15 to the function executing unit 10. In this case, in the switch arrangement step, the magnetic switch 14 which inputs a control signal to the latch circuit as the state holding circuit is disposed in the capsule casing 16 of the capsule endoscope 3, which is tubular and rotationally symmetric in shape with respect to the longitudinal axis t direction, such that the extending direction D1 is substantially aligned with the longitudinal axis t direction.

In the power supply step, the magnet 6 is moved to the magnetic switch 14 from the outside of the capsule endoscope 3 so as to align the direction of the magnetic field generated by the magnet 6 with the longitudinal axis t direction of the capsule casing 16. The fixed electrode 14d and the movable electrode 14e of the magnetic switch 14 are magnetized such that the surfaces of those electrodes, which face each other, have different magnetic polarities (S and N polarities) in accordance with the magnetic induction action of the magnetic field generated by the magnet 6, which acts substantially in parallel with the longitudinal axis t direction (viz., substantially perpendicular to the contact/separation direction D2). By the magnetization of these electrodes, the movable electrode 14e moves toward the fixed electrode 14d by attraction and comes in contact with the fixed electrode 14d. A control signal generated as the result of contacting of those electrodes is input to the latch circuit as the state holding circuit. As a result, the latch circuit controls the electric power supply from the power source unit 15 to the function executing unit 10. By the control by such a latch circuit, a state of the power supply from the power source unit 15 to the function executing unit 10 is retained.

Thus, in the embodiment, the magnet 6 located outside the capsule endoscope 3 is moved close to the magnetic switch 14 in the longitudinal axis t direction, and the movable electrode 14e is moved and brought into contact with the fixed electrode 14d by the action of the magnetic field L generated by the magnet 6, which acts in the direction substantially perpendicular to the extending direction of the magnetic switch 14 (more specifically, extending direction D1 of the fixed electrode 14d). As a result, electric power can be supplied from the power source unit 15 to the function executing unit 10. Therefore, it is easy to define the approximation position and direction of the magnet 6 when the magnet 6 is moved close to the capsule endoscope 3 for the contact/separation operation (i.e., on/off switching operation of the power source) of the magnetic switch 14. As a consequence, there is no need of moving a magnetic body for causing the contact/separation of the reed switch to the capsule endoscope while aligning with the reed extending direction, which is inevitably performed when the reed switch is used for the capsule endoscope. Accordingly, the capsule endoscope is easily started to operate without seeking the magnetic field direction of the magnetic body with respect to the extending direction of the magnetic switch by relatively rotating the capsule casing and the magnetic body.

First Modification

Figure 9:
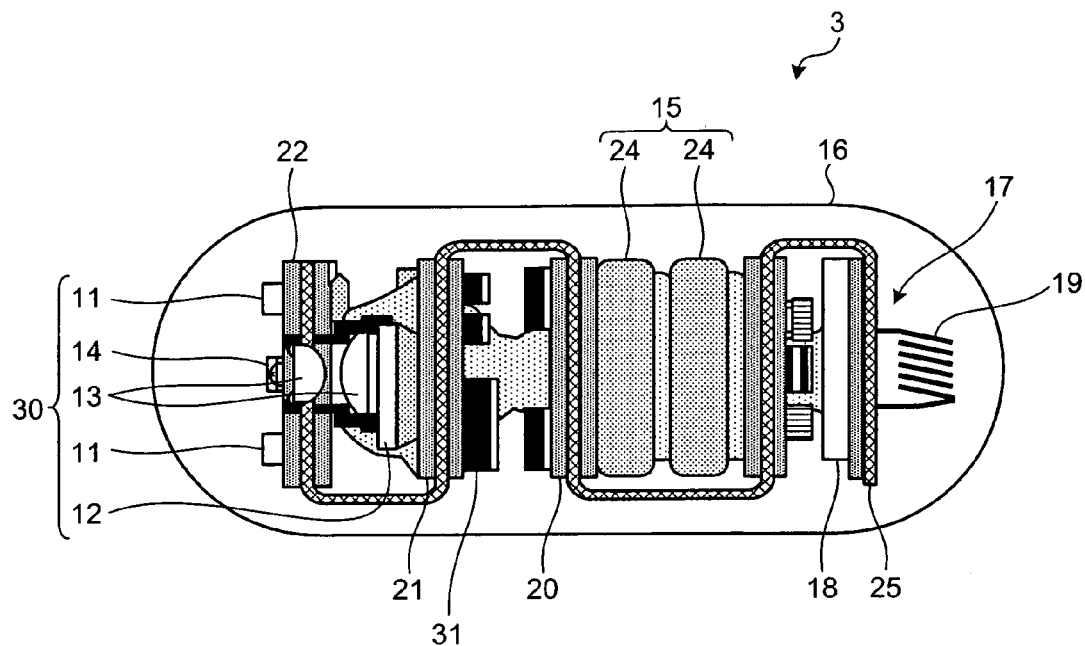
FIG. 9 is a cross sectional view showing an internal configuration of a first modification of the capsule endoscope according to the invention.

FIG. 9 is a cross sectional view showing an internal configuration of a first modification of the capsule endoscope according to the invention. While the magnetic switch 14 is provided on the surface of the switch board 20 at a position near the power source unit 15 in the first embodiment, it is provided on the surface of the illumination board 22 on which the LEDs 11 are provided, in the first modification.

The first embodiment has the same useful effects as those of the first embodiment. Further, the magnetic switch 14 is located out of the illumination range of the LEDs 11 and a visibility range determined by the optical characteristics of the image forming lens of the optical system device 13. Optical flare by the image sensor 30 never occurs, and good image pickup is secured.

Second Modification

Figure 10:
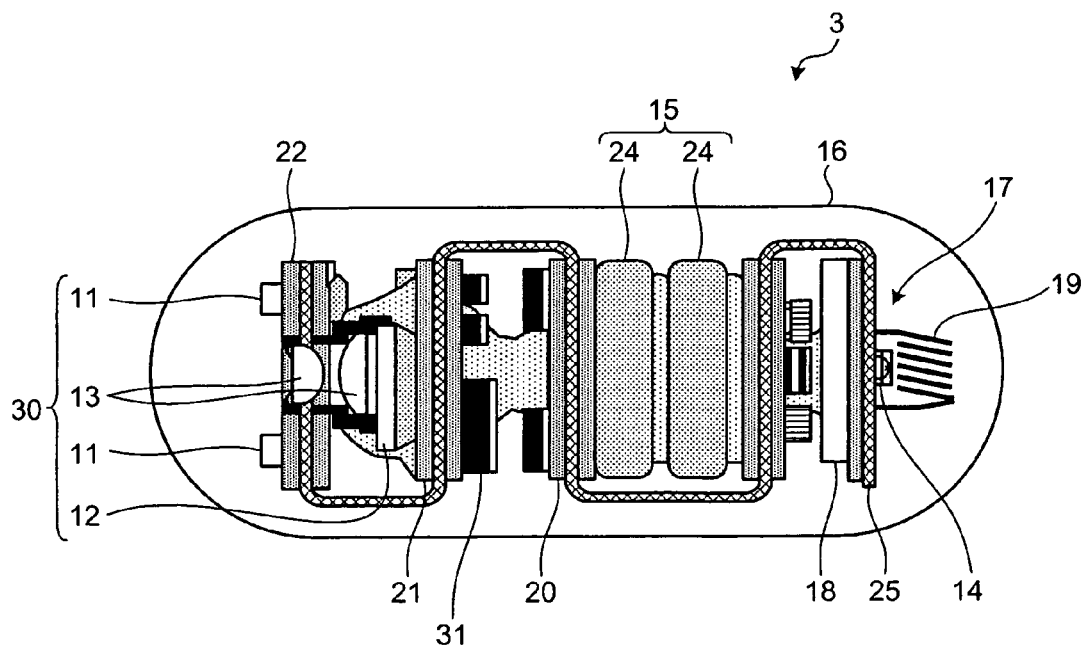
FIG. 10 is a cross sectional view showing an internal configuration of a second modification of the capsule endoscope according to the invention.

FIG. 10 is a cross sectional view showing an internal configuration of a second modification of the capsule endoscope according to the invention. In the modification, the magnetic switch 14 is provided on the surface of the radio board 25 including the antenna 19 and under the antenna 19.

In the second modification 2 has the same useful effects as those of the first embodiment. Further, the magnetic switch 14 is disposed in the spatial area having no wiring under the coil antenna 19. In this respect, the area of the radio board 25, which is not used, is effectively used. The magnetic switch 14 of the invention is small. Accordingly, it may be installed at any position except that the boards and the locations where the components are located. Also in the modification, the magnet 6 may be moved toward the magnetic switch from the leading end of the capsule endoscope 3 containing the image sensor 30 or the trailing end thereof containing the radio unit 17, according to strength of the magnetic field.

In the body-insertable apparatus and the power supplying method therefor according to the present invention, a conduction state and a non-conduction state are switched through the magnetic induction action of the magnetic body disposed in the longitudinal axis direction of the capsule casing. Accordingly, the capsule endoscope is easily started to operate.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

INDUSTRIAL APPLICABILITY

As seen from the foregoing description, the body-insertable apparatus and the power supplying method therefor according to the present invention, are useful in acquiring in-vivo information such as body cavity images. In particular, the invention is suitable for a body-insertable apparatus which introduces into a subject a capsule endoscope which is easily started to operate by moving a magnetic body close to a magnetic switch located within a capsule casing, and a power supplying method therefor.

What is claimed is:

1. A body-insertable apparatus comprising:
a function executing unit which executes a predetermined function;
a power source unit which supplies electric power to the function executing unit;
a capsule body which contains the function executing unit and the power source unit; and
a magnetic switch which is provided in the capsule body, and controls the power supply from the power source unit to the function executing unit by a pair of contacts, the pair of contacts being brought into contact with or separated from each other by a magnetic field, the magnetic field being applied from the outside of the capsule body in a direction substantially parallel to a longitudinal axis direction of the capsule body, wherein
the function executing unit comprises an illuminating unit, an imaging unit and a radio transmitting unit; and
the magnetic switch is mounted on a board on which one of the illuminating unit and the radio transmitting unit is mounted, the board being perpendicular to a central axis of the capsule body.

2. The body-insertable apparatus according to claim 1, wherein
the magnetic switch is provided on a board on which the illuminating unit is mounted.

3. The body-insertable apparatus according to claim 1, wherein
the magnetic switch is provided on a board on which the radio transmitting unit is mounted.

4. A body-insertable apparatus comprising:
a function executing unit which executes a predetermined function and includes at least an imaging unit for imaging a body cavity;
a power source unit which supplies electric power to the function executing unit;
a switch unit which disconnectively connects the function executing unit and the power source unit; and
a capsule body which is tubular and rotationally symmetric with respect to a longitudinal axis direction, and contains the function executing unit, the power source unit, the switch unit, and an imaging board on which the imaging unit is mounted;
wherein the switch unit comprises a base seat, a fixed electrode, a movable electrode and a pair of electrodes, the fixed electrode and the movable electrode each being made of a conductive and magnetic material and each being provided on a surface of the base seat, the pair of electrodes being provided on a reverse side of the base seat and electrically connected to the fixed electrode and the movable electrode, respectively, the fixed electrode and the movable electrode being brought into contact with or separated from each other by a magnetic field applied in a contact and separation direction of the fixed electrode and the movable electrode; and
the switch unit controls the power supply from the power source unit to the function executing unit in accordance with an action of a magnetic field, the magnetic field being applied from the outside of the capsule body in a direction substantially parallel to the longitudinal axis direction.

5. The body-insertable apparatus according to claim 4, wherein
each of said movable and fixed electrodes are magnetized to have different magnetic polarities stacked in a thickness direction by an action of a magnetic field applied from the outside of the capsule body substantially parallel to the longitudinal axis direction, and the movable electrode moves to contact the fixed electrode when the movable electrode is magnetized to have different magnetic polarities stacked in the thickness direction.

6. The body-insertable apparatus according to claim 5, further comprising a state holding circuit which holds a state of the power supply from the power source unit to the function executing unit in accordance with a signal from the magnetic switch, wherein the magnetic switch controls the power supply from the power source unit to the function executing unit in accordance with an output from the state holding circuit.

* * * * *